US007794459B2

(12) United States Patent
Faure

(10) Patent No.: US 7,794,459 B2
(45) Date of Patent: Sep. 14, 2010

(54) FLEXIBLE ENDOSCOPE FOR ENDO LUMINAL ACCESS RADIAL FREQUENCY TUMOR ABLATION

(75) Inventor: André S. Faure, Besancon (FR)

(73) Assignee: Trod Medical, Besancon (FR)

( * ) Notice: Subject to any disclaimer, the term of this patent is extended or adjusted under 35 U.S.C. 154(b) by 548 days.

(21) Appl. No.: 11/571,082

(22) PCT Filed: Jun. 23, 2005

(86) PCT No.: PCT/IB2005/001774

§ 371 (c)(1),
(2), (4) Date: Feb. 8, 2007

(87) PCT Pub. No.: WO2006/000888

PCT Pub. Date: Jan. 5, 2006

(65) Prior Publication Data

US 2009/0163906 A1    Jun. 25, 2009

Related U.S. Application Data

(60) Provisional application No. 60/582,449, filed on Jun. 23, 2004.

(51) Int. Cl.
*A61B 18/14* (2006.01)
(52) U.S. Cl. .............................. 606/41; 606/45; 606/46; 606/48
(58) Field of Classification Search .................. 606/46, 606/48, 50, 41
See application file for complete search history.

(56) References Cited

U.S. PATENT DOCUMENTS

| 4,699,157 | A | * | 10/1987 | Shonk .......................... 607/122 |
| 5,688,267 | A | * | 11/1997 | Panescu et al. ................. 606/41 |
| 5,873,877 | A | * | 2/1999 | McGaffigan et al. ........... 606/41 |
| 6,086,583 | A | | 7/2000 | Ouchi |
| 6,258,087 | B1 | * | 7/2001 | Edwards et al. ................ 606/41 |
| 6,385,472 | B1 | * | 5/2002 | Hall et al. ..................... 600/374 |
| 6,464,697 | B1 | | 10/2002 | Edwards |
| 6,974,455 | B2 | * | 12/2005 | Garabedian et al. ........... 606/41 |

* cited by examiner

*Primary Examiner*—Lee S Cohen
*Assistant Examiner*—Jaymi Della
(74) *Attorney, Agent, or Firm*—Schmeiser, Olsen & Watts, LLP

(57) ABSTRACT

A radio frequency (RF) treatment flexible endoscope, for the in depth destruction of tumors by endo luminal access, like in a lung, esophagus, colon, rectum, etc . . . The electrodes (2',2") working in bipolar mode, deploy laterally and in parallel from the endoscope main body (1), reaching a tumor deeply located in the organ parenchyma. The use of different disposable distal end portions (15) of the endoscope allows the deployment of the electrodes (2',2") at different distances one from each other, in order to fit the destruction are to the tumor's size and shape. The deployment of the parallel electrodes (2',2") from the endoscope's main body (1) is controlled by motor drives (4) or a mechanical handled system (3), in order to reach the tumor with near a millimeter precision. In order to fix the endoscope's distal end to the tissue, so to allow a perfect parallel deployment of the electrodes, an inflating cuff (5) is placed at the opposite side of the distal end, as well as a suction system, with its holes (21) placed near the electrodes' deployment location. An external RF generator and a imaging system are associated to the use of the device.

11 Claims, 17 Drawing Sheets

FLEXIBLE ENDOSCOPE FOR ENDO LUMINAL ACCESS RADIAL FREQUENCY TUMOR ABLATION

CONTINUING APPLICATION DATA

This application is a 371 of PCT/IB05/01774 filed Jun. 23, 2005 which claims benefit of U.S. Provisional Patent Application Ser. No. 60/582,449 filed Jun. 23, 2004 and entitled "Endocavitary access flexible and adjustable endoscope for tumor ablation using radio frequency", by Faure A. which is incorporated herein by reference.

BACKGROUND OF THE INVENTION

1. Field of Invention

The present invention relates to endoscopic surgery, more specifically, to an endoscopic flexible device, able to ablate (destruct) a tumor, using radio frequency, by an endo luminal access.

2. Description of the Related Art

Since the beginning of endo luminal endoscopy, the major concern was mainly having a new diagnostic mean. In fact, using a light source and introducing a camera in a endocavity allowed early diagnostic in several types of cancer (lungs, stomach, etc . . . ).

As the technique improved, some endoscopes offered a central canal, allowing the endo luminal introduction of biopsy clamps and even some rudimentary coagulation devices. At the same time, the development and the improvement of flexible endoscopes allowed to go deeper and safer in some organs, like the lungs, colon, etc . . .

However, even with the improvement of all the diagnostic means and with a globally earlier detection of cancer, classic surgical technique remained the major cancer treatment choice.

More recently, some new endoscopic devices introduced some new therapeutic approaches, but still inadequate for an effective tumor resection and destruction.

In some new devices, different physical methods have been disclosed, as radio frequency, ultrasound, laser beams, etc . . . , in order to deal with cancer. Radio frequency has, however, the biggest experimental basis.

For example, the U.S. Pat. No. 4,920,978 and No. 6,238,392 as well as patent applications n 20050131402, n 20050107829 and n 20040230190 describe flexible endoscopes using radio frequency for endo luminal treatment, but are unable to penetrate deeply in the tissue and are limited to surface treatment. This problem is particularly limiting in the lungs, where a tumor can obstruct an airway and, at the same time, spread deeply in the pulmonary parenchyma. In addition, these devices' electrodes are unable to adapt to a tumor shape and, consequently, cannot guarantee the destruction of deeply spread tumors.

U.S. Patent Application n 20050033279 discloses a radio frequency ablation device for tumor destruction. However, it does not allow a flexible endo luminal access, obliging the operator to penetrate through the patient's skin to reach the tumor, causing important bleeding and surrounding tissue damage. Moreover, the electrodes described are placed at the tip of a handle, not allowing it to access tumors laterally, from a non tumor obstructed lumen.

There is a need for a device allowing the destruction of a tumor from a endo luminal access, adapting the destruction to the tumor's size and shape, and being able to reach in depth spread tumors, from a non tumor obstructed lumen.

SUMMARY OF THE INVENTION

Accordingly, the aim of the invention is to provide a medical flexible endoscope and the procedure to do the ablation (i.e. destruction), using radio frequency, of a tumor, located near or in an endo lumen, as the bronchial tree, the oesophagus, the rectum, the colon, etc . . .

A further object of the invention is to provide a device able to destroy, using radio frequency, a specific and defined tumoral region, penetrating in the patient's body from an endo luminal access, as the bronchial tree, the esophagus, the rectum, the colon, etc . . .

Still an object of the invention is to provide a device able to access and destroy a in depth tumor, through a natural endo lumen, as the airways, the oesophagus, the colon and the rectum.

A further object of the present invention if to provide a RF tumor ablation (i.e. destruction) device which includes an elongated and flexible main body, a distal end emerging bipolar parallel electrodes, made up of two flexible and elongated wires activated by an external radio frequency generator, a proximal handle to control the movements of the main body, a near proximal placed control box, to control the deployment of the electrode's two wires, and a near terminal placed cuff.

In an additional embodiment of the invention, the control box comprises motor drives, capable of controlling with great precision the sliding movement inside the main body and the deployment in the tissue of the electrode's two wires.

In another embodiment of the invention, The terminal end of the device's main body also comprises a removable and disposable part, replaced before each intervention, through which the electrode's two wires deploy into the tissue, exiting each by an exiting hole.

In a further embodiment of the invention, different disposable parts, with different spacing between the two exiting holes can be placed on the terminal end of the main body, allowing the two wires to protrude at different distance one of each other.

In an additional embodiment of the invention, the two electrode's wires slide in the main body and in the disposable part crossing tightly two internal canals, one canal for each wire. The canals of the disposable part adapt exactly to the main body's canals, so to allow each wire to slide easily from the main body to the disposable part, before protruding in the tissue.

Still, in an additional embodiment, the electrode's two wires are disposable, in which case they are replaced before each intervention, and removed after each procedure.

Still in a further embodiment of the invention, the terminal cuff is replaced or combined with some external holes, placed near the electrode's exit holes, linked to an external negative pressure generator (as a pump), in order to fix the device's head to the tissue.

DETAILED DESCRIPTION OF THE PREFERRED EMBODIMENTS

Figure 1:
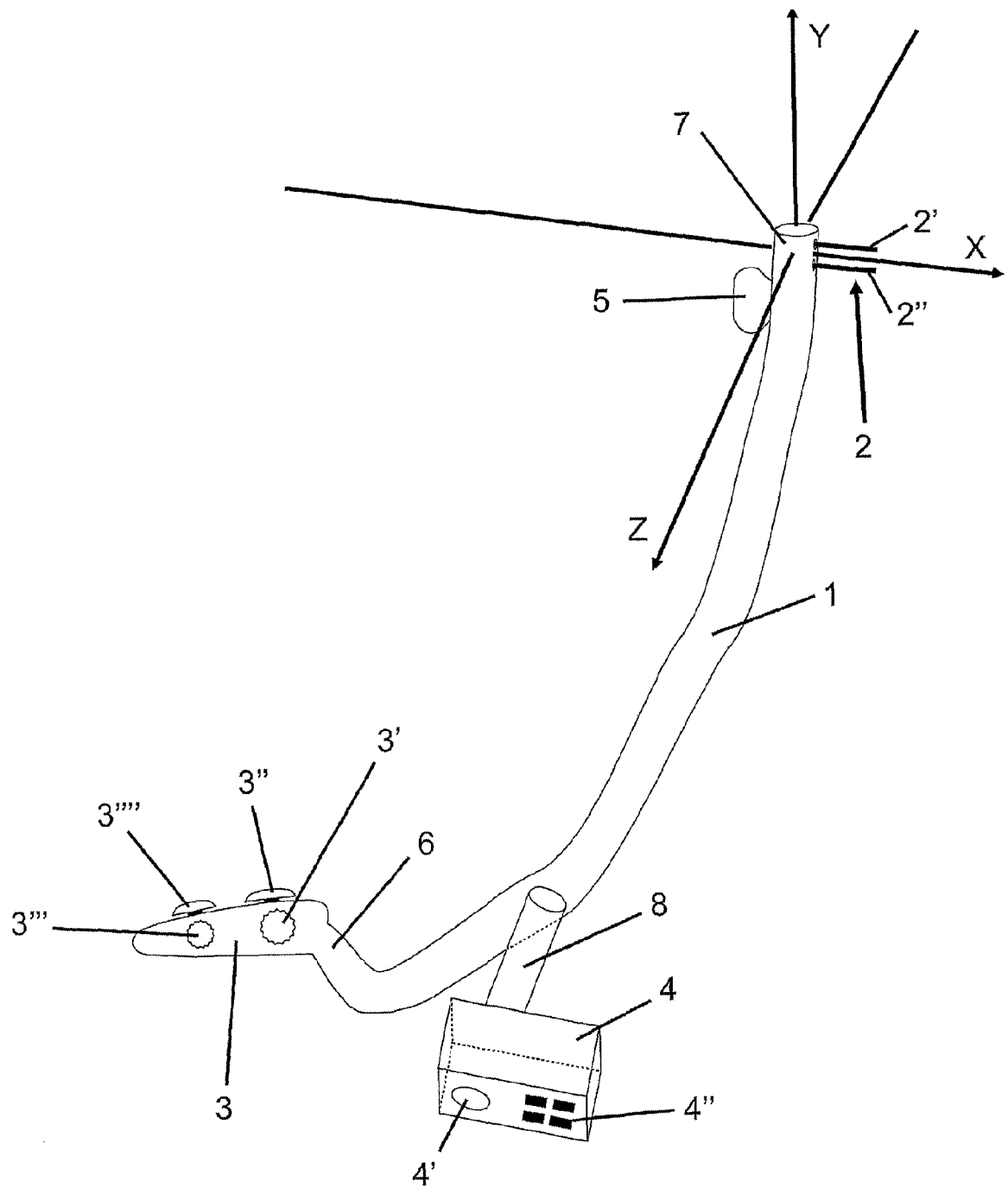
FIG. 1 represents an overall view of the medical device, according to the present invention.

As illustrated on FIG. 1, the medical device according to the invention comprises as elements a main body 1, a handle 3, a control box 4 and a bipolar electrode 2.

The bipolar electrode 2 has typically two flexible wires 2' and 2", but can have a different number of wires.

The main body 1 has a proximal end 6 and a distal end 7.

The main body 1 is an elongated and cylinder shaped flexible tube, of a total length between 30 cm and 80 cm, roughly.

The distal end 7 of the main body 1 has, roughly, a diameter between 4 and 15 mm.

Figure 13:
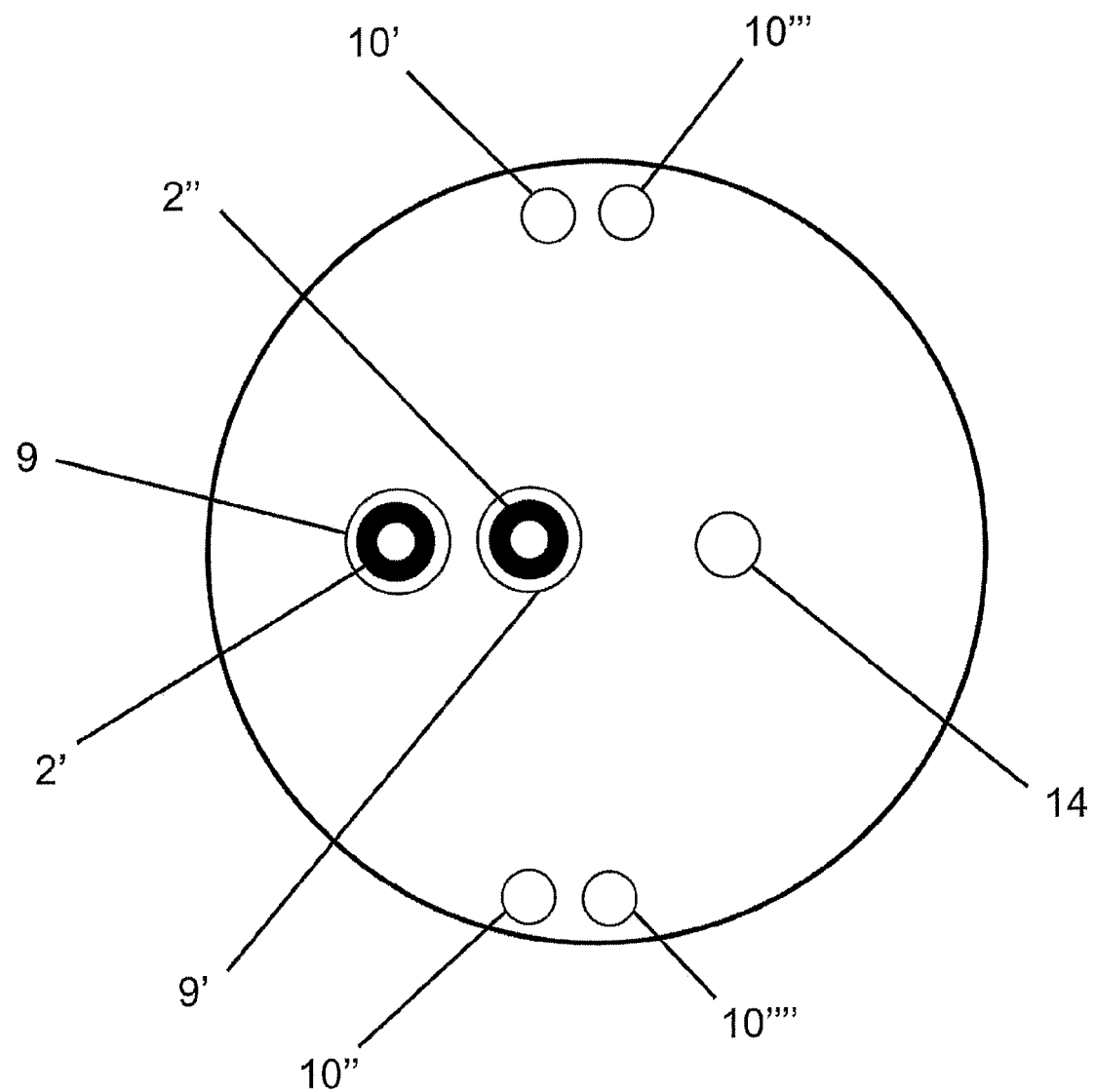
FIG. 13 represents a cross section of the middle of the main body, showing the structures crossing it.

The control box 4 is connected to the main body 1 via the motor box tube 8. The control box 4 can be disconnected from the motor box tube 8, allowing the main body 1, as well as the motor box tube 8, to be cleaned and sterilized before each procedure, FIG. 13 shows a cross section of the main body 1 where we can see the following components crossing the main tube from the proximal end 3 to the distal end 7: more internally, two canals 9 and 9', in which the electrode's 2 two flexible wires 2' and 2" slide, more externally, the two cables 10' and 10", which control the said mobility 1, the two cables 10''' and 10'''', which control the said mobility 2, and the air way 14, allowing the cuff 5 to be inflated.

Figure 17:
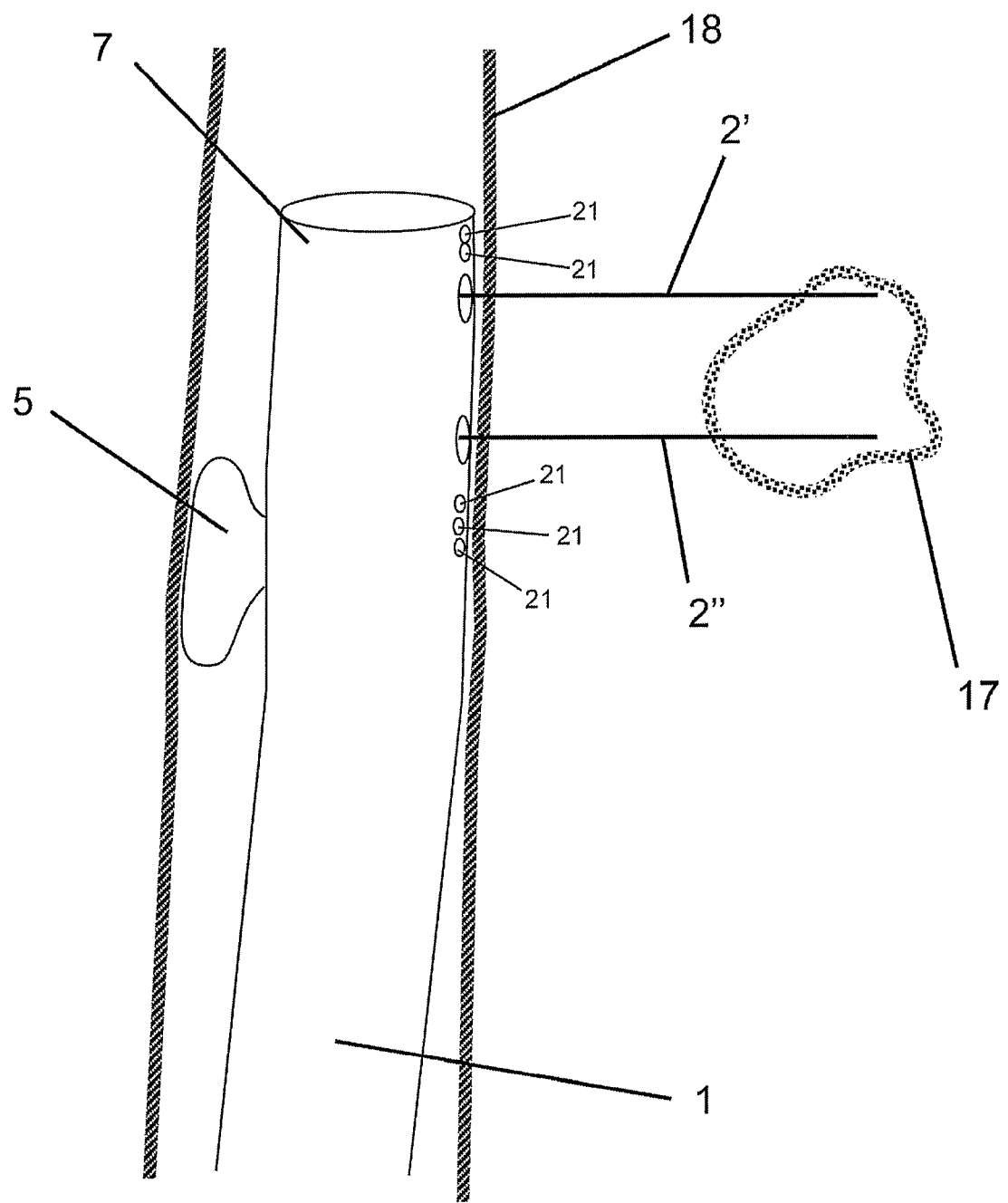
FIG. 17 represents the endoscope in operating position, with its electrode's wires inserted inside a tumor and the fixing holes, placed near the electrodes' exiting holes.

In another preferred embodiment, the cross section of the main body 1 also has an air pipe, linking the fixing holes 21, as shown in FIG. 17, to an external negative pressure generator, as a pump.

In another preferred embodiment, the cross section of the main body 1 also has an optic conduction way, linking an optical system to the distal end 7 of the main body 1.

In another preferred embodiment, the motor box is replaced by mechanical and manually activated drives, located in the handle 3.

Figure 2:
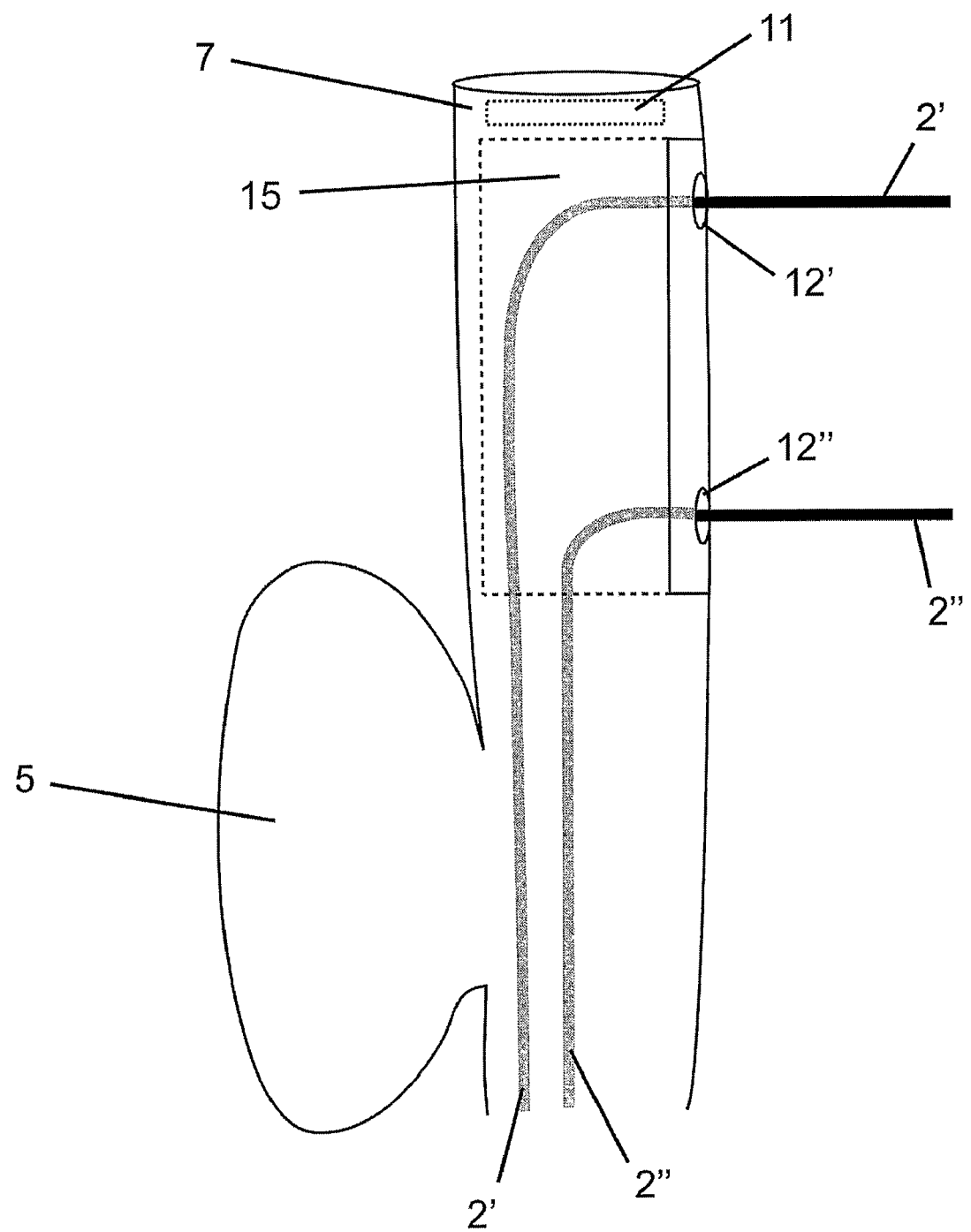
FIG. 2 represents said medical device, more precisely its terminal end, with the bipolar electrode deployed, the counter lateral placed cuff and the delimitation of the disposable part. The distance between the two wires is here maximum.

FIG. 2 shows, externally, the distal end 7 of the main body 1, with its cuff 5 and the electrode's 2 two flexible wires 2' and 2" exiting from the main body 1 by the two exiting holes 12' and 12". The cuff 5 and the two holes 12' and 12" are placed in opposite sides of the main body 1.

FIG. 2 also shows, internally, i.e. inside the main body 1, a magnetic coil 11, used to identify the position of the distal end 7 by a navigation system, the disposable part 15 and the electrode's 2 two wires 2' and 2".

In another preferred embodiment, the magnetic coil 11 is replaced by an optic system, allowing the operator to see the endo lumen, via a transmission way as fiberoptic.

The cuff 5 can be inflated by air insertion from the control box 4 trough the airway 14, under a command by the operator done in control panel 4".

The cuff 5 is used to apply the two exiting holes 12' and 12" against the endo lumen wall 18, as shown in picture 10.

In another preferred embodiment, as shown in FIG. 17, one or several holes 21 are placed near the electrodes' exiting holes 12' and 12", and are linked to an external negative pressure generator, as a pump, in order to apply the exiting holes 12' and 12" against the endo lumen wall 18.

The bipolar electrode's 2 two wires 2' and 2" are, before each procedure, inserted in the insertion point 4' of the control box 4, and slide inside the two canals 9 and 9', in the direction of the distal end 7, cross the two canals 9 and 9' also present in the disposable part 15, until they protrude outside the main body 1 by crossing the exiting holes 12' and 12".

Preferably, before each procedure, the wires 2' and 2" are inserted in the insertion point 4' sterilized, as well as the main body 1 has been previously cleaned and sterilized.

Preferably, the up sliding movement of the two wires 2' and 2", towards the distal end 7, are done under control of motor drives placed inside the control box 4, after a command done by the operator in the control panel 4".

The two wires 2' and 2" are cylinder shaped, flexible and made of a metallic material, preferably made of nitinol, for its super elastic properties.

The diameter of the two wires 2' and 2" vary between 0.2 mm and 1 mm.

Figure 14:
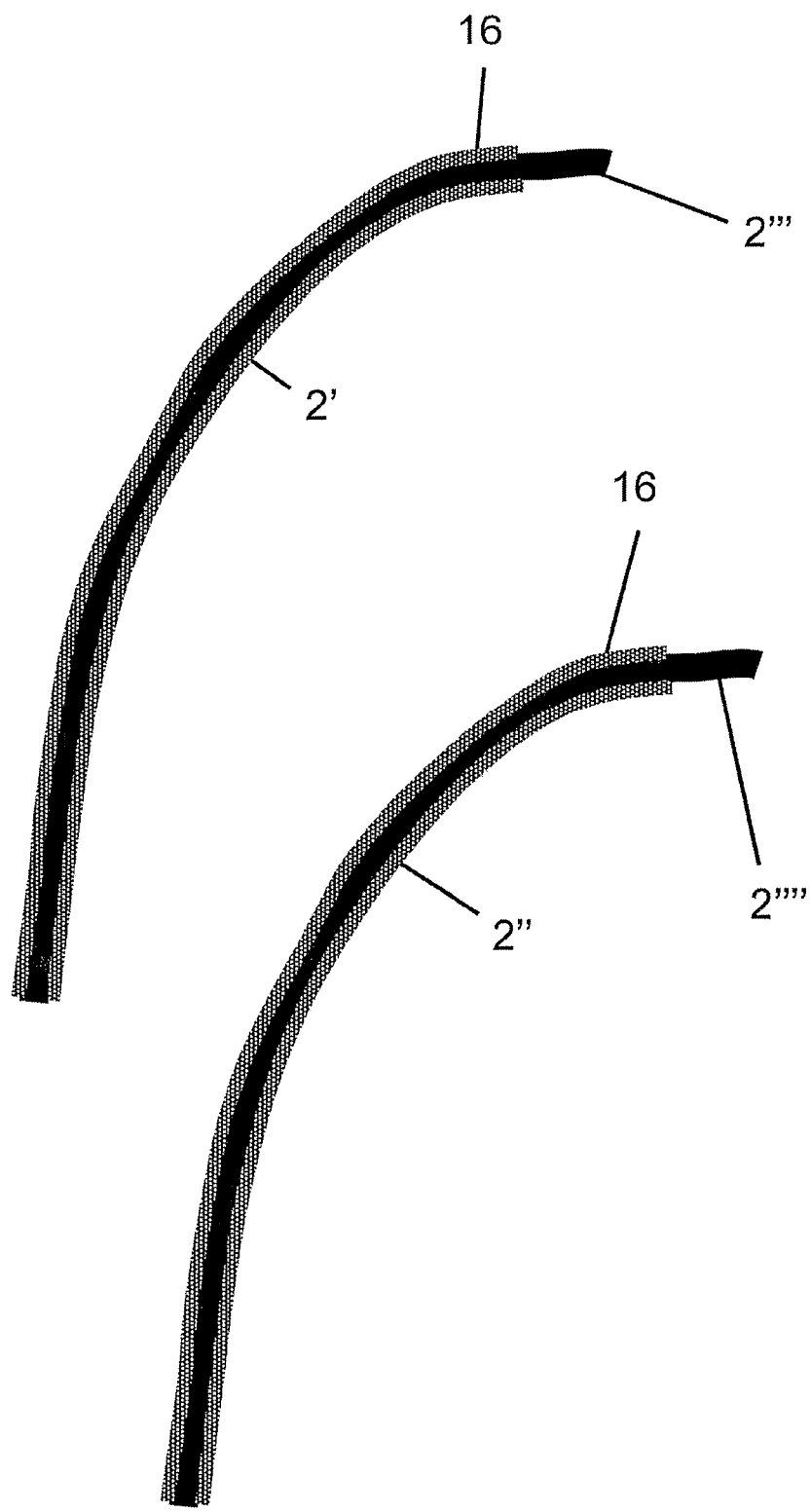
FIG. 14 represents the electrode's 2 wires, with their polymeric encapsulation and terminal active portions.
Figure 15:
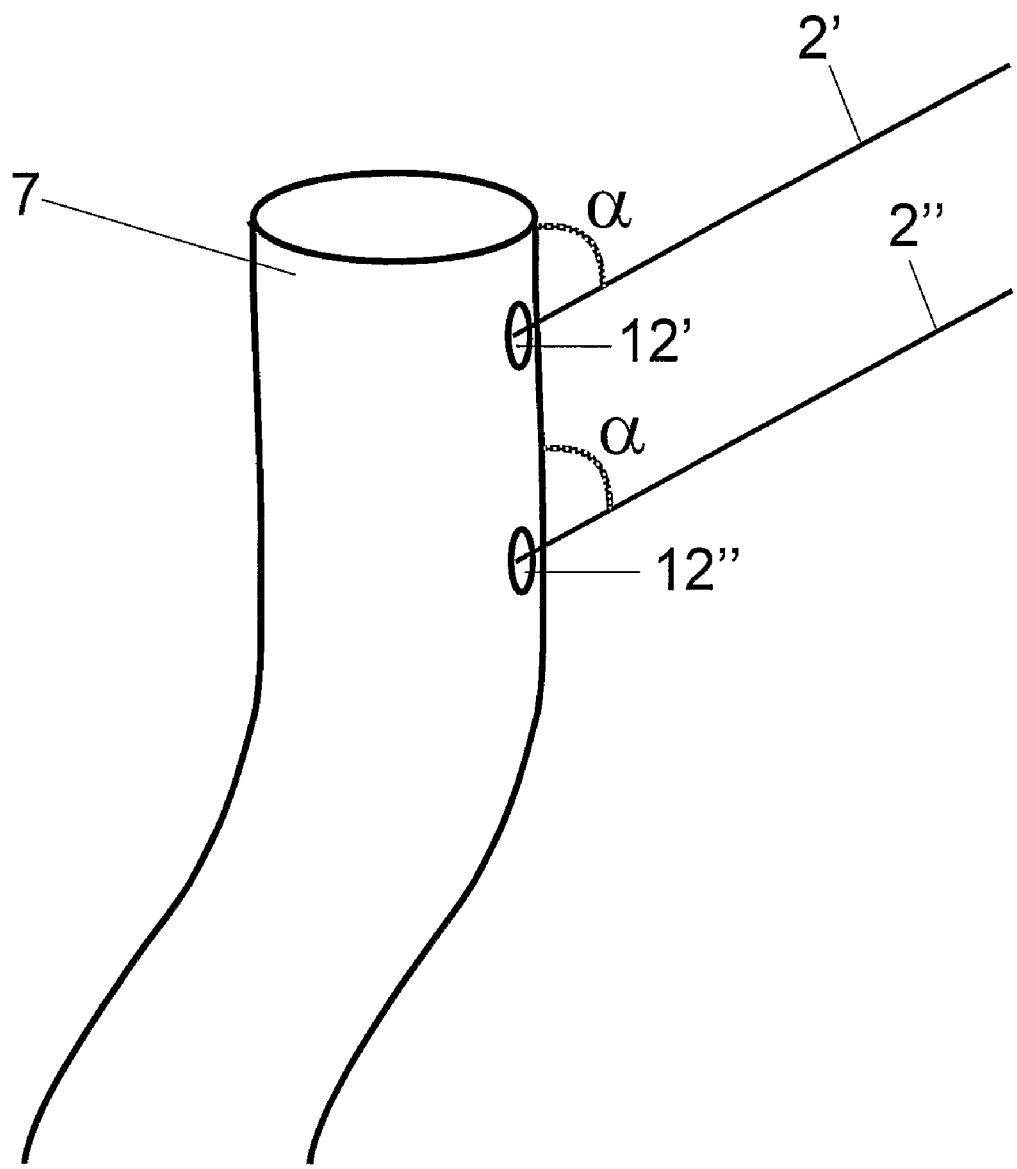
FIG. 15 represents the device's main body, with the 2 electrodes' wires deployed, both with the same angle with the main body.
Figure 16:
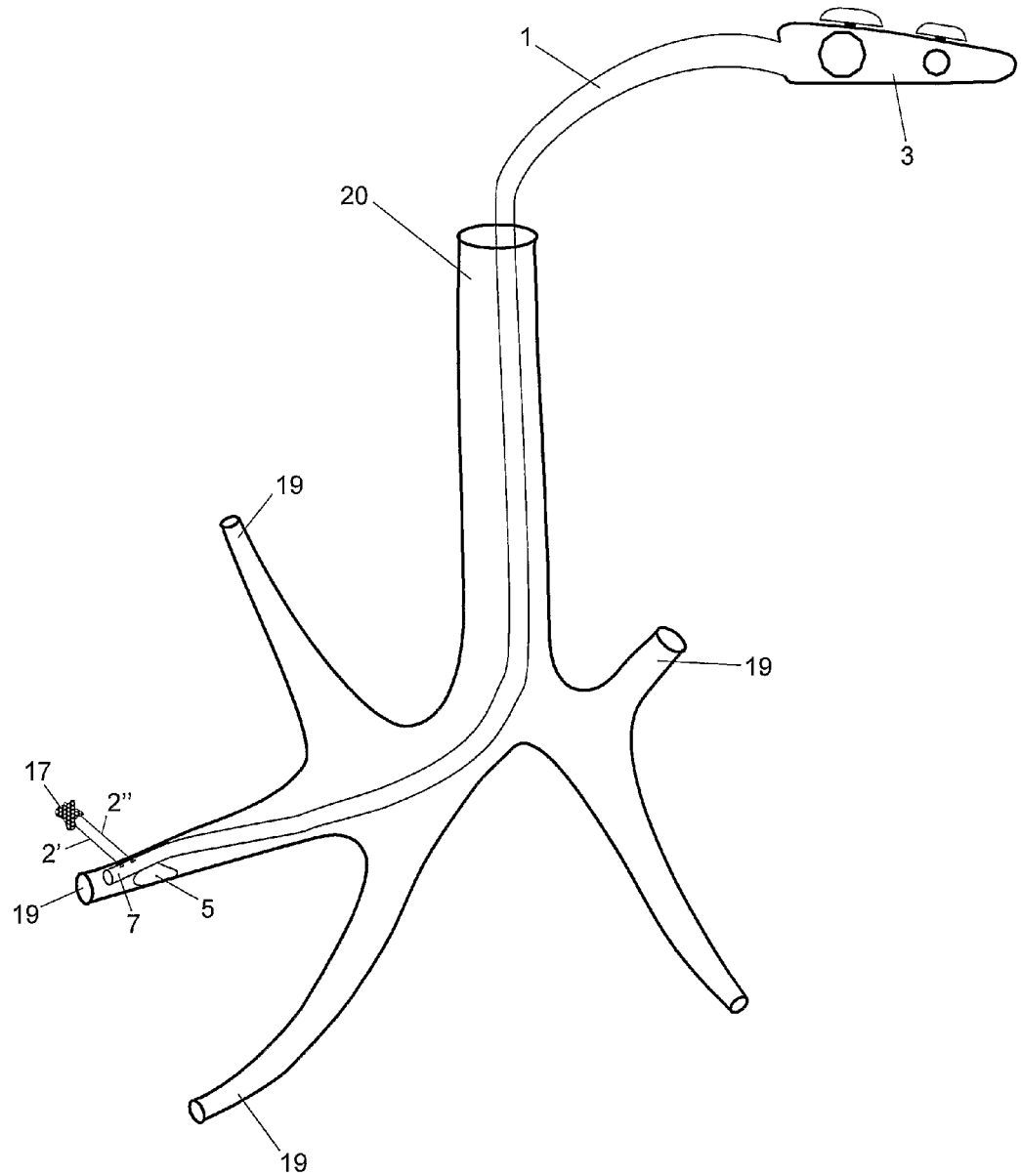
FIG. 16 represents the device, inserted in the bronchial tree by the trachea and its electrodes' wires reaching a tumor located in the pulmonary parenchyma.

As showed in FIG. 14, the major part of the wires 2' and 2" length is encapsulated by a insulating polymeric material 16, and only the distal part 2''' and 2'''' of each wire 2' and 2" respectively, i.e. a fraction of the part of each wire 2' and 2" that protrudes outside the main body 1 through the exiting holes 12' and 12", are not encapsulated.

The two wires 2' and 2" are activated by an external medical use radio frequency generator, and, then, a electric or electromagnetic current flows through the two wires 2' and 2". However, only the non encapsulated distal parts 2''' and 2'''' of the wires 2' and 2" respectively, are active and are heated by the activation of the external radio frequency generator.

The non encapsulated distal part 2''' and 2'''' of the wires 2' and 2" respectively, have a variable length, to allow different sizes of tumors to be destroyed by the heating effect. Typically, the non encapsulated distal part 2''' and 2'''' have a length varying between 5 mm and 30 mm.

Preferably, for each intervention, the non encapsulated distal part 2''' and 2'''' of the wires 2' and 2'' have identical lengths.

Figure 3:
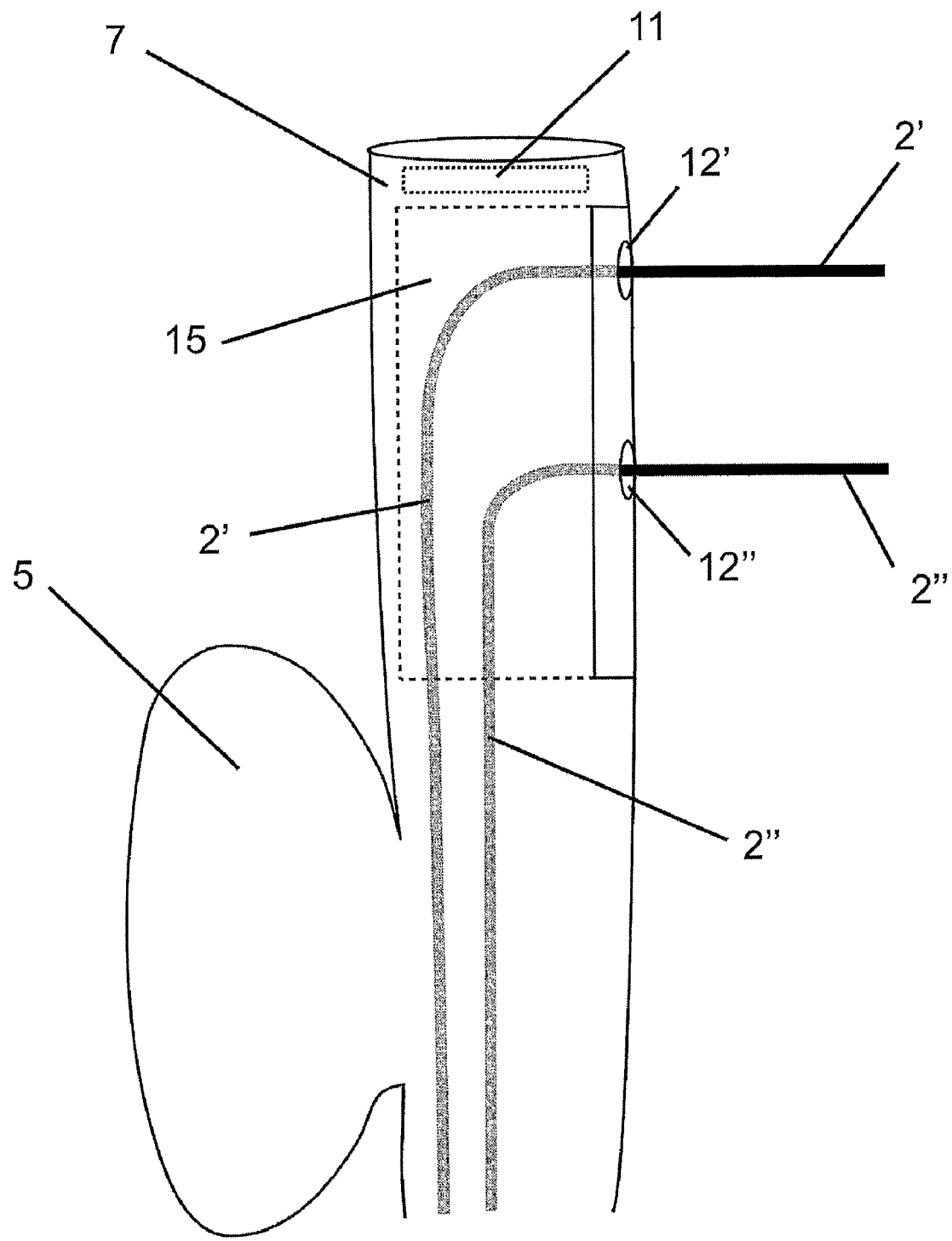
FIG. 3 represents the same as FIG. 2, but with another disposable part in place, with an intermediate distance between the electrode's two wires.
Figure 4:
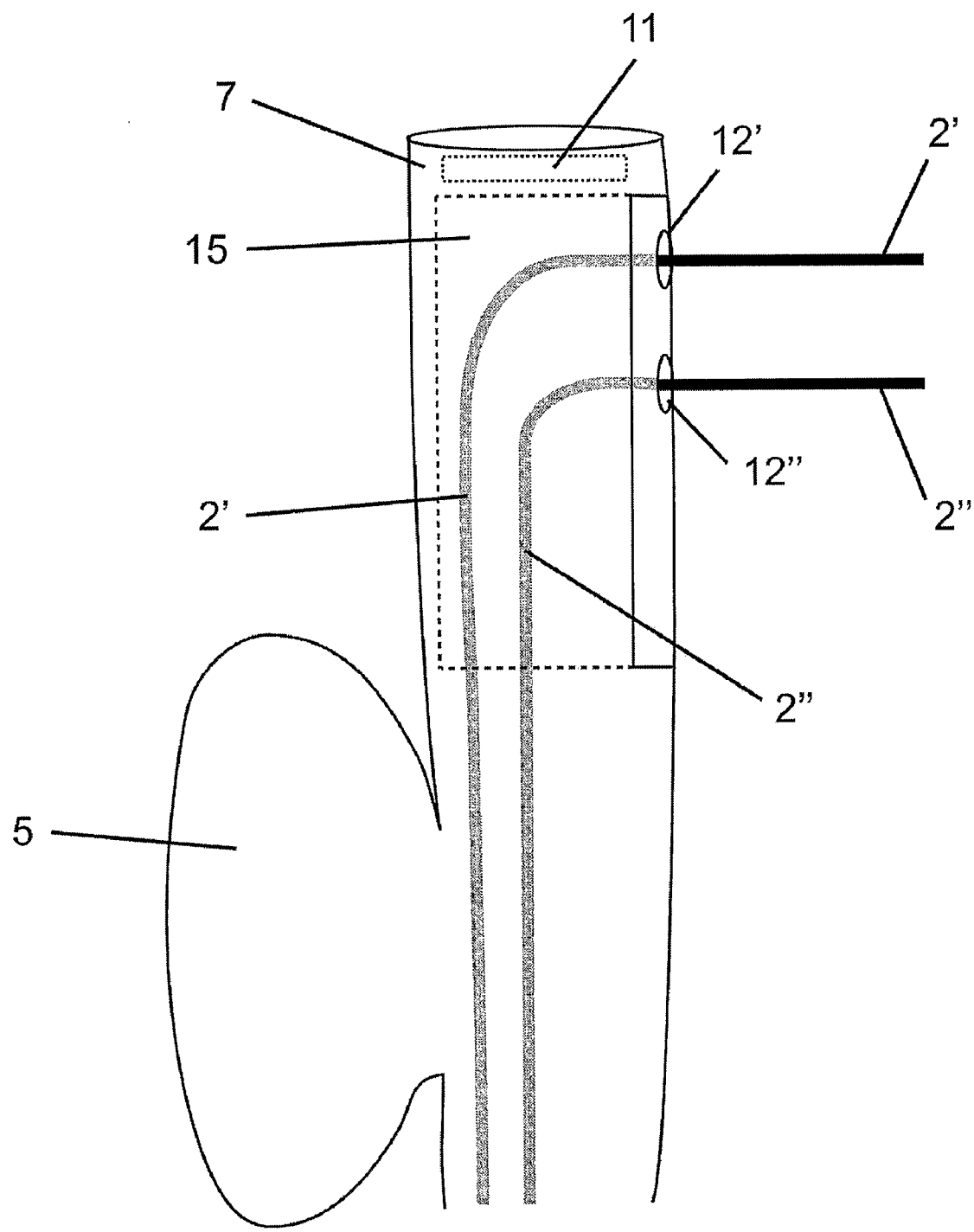
FIG. 4 represents the same as FIGS. 2 and 3, but with a new disposable part in place, with a minimal distance between the two wires.

FIG. 2, FIG. 3 and FIG. 4 show the distal end 7 of the main body 1, with its cuff 5, the disposable part 15 inserted in the main body 1, and the electrode's 2 two wires 2' and 2'' exiting from the main body 1 by the exiting holes 12' and 12'', respectively, but with a difference of the distance between the two exiting holes 12' and 12''. This distance between the two exiting holes 12' and 12'' allows different sizes of tumors to be destroyed by the heating effect generated between and around the two distal parts 2''' and 2'''' of the two wires 2' and 2'', respectively, when a external radio frequency generator, linked to the two wires 2' and 2'', is activated.

Typically, the distance between the two exiting holes 12' and 12'' can vary between 5 mm and 30 mm.

Figure 5:
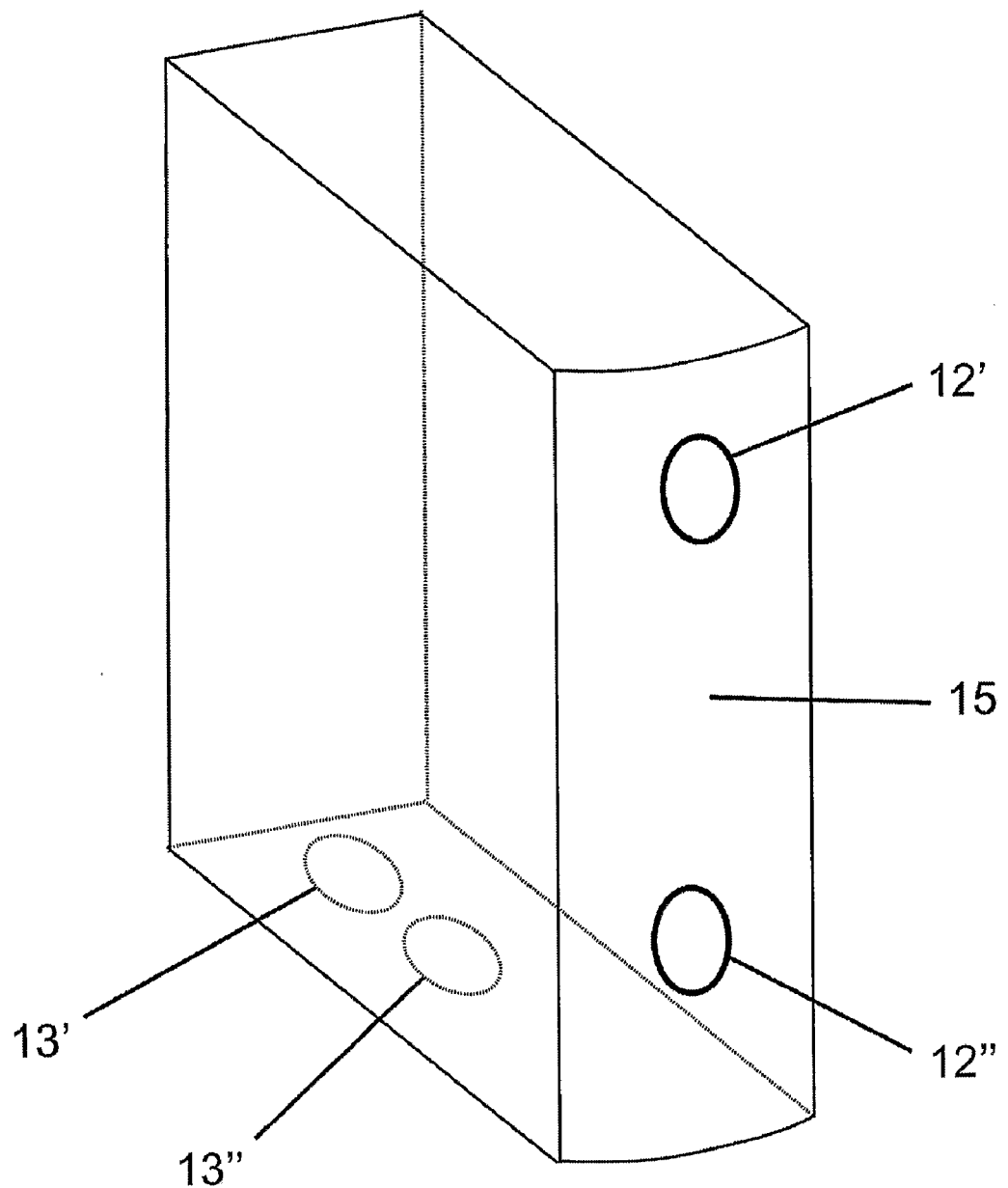
FIG. 5 represents the disposable part with a maximal distance between the two exiting holes of the electrode's wires.
Figure 6:
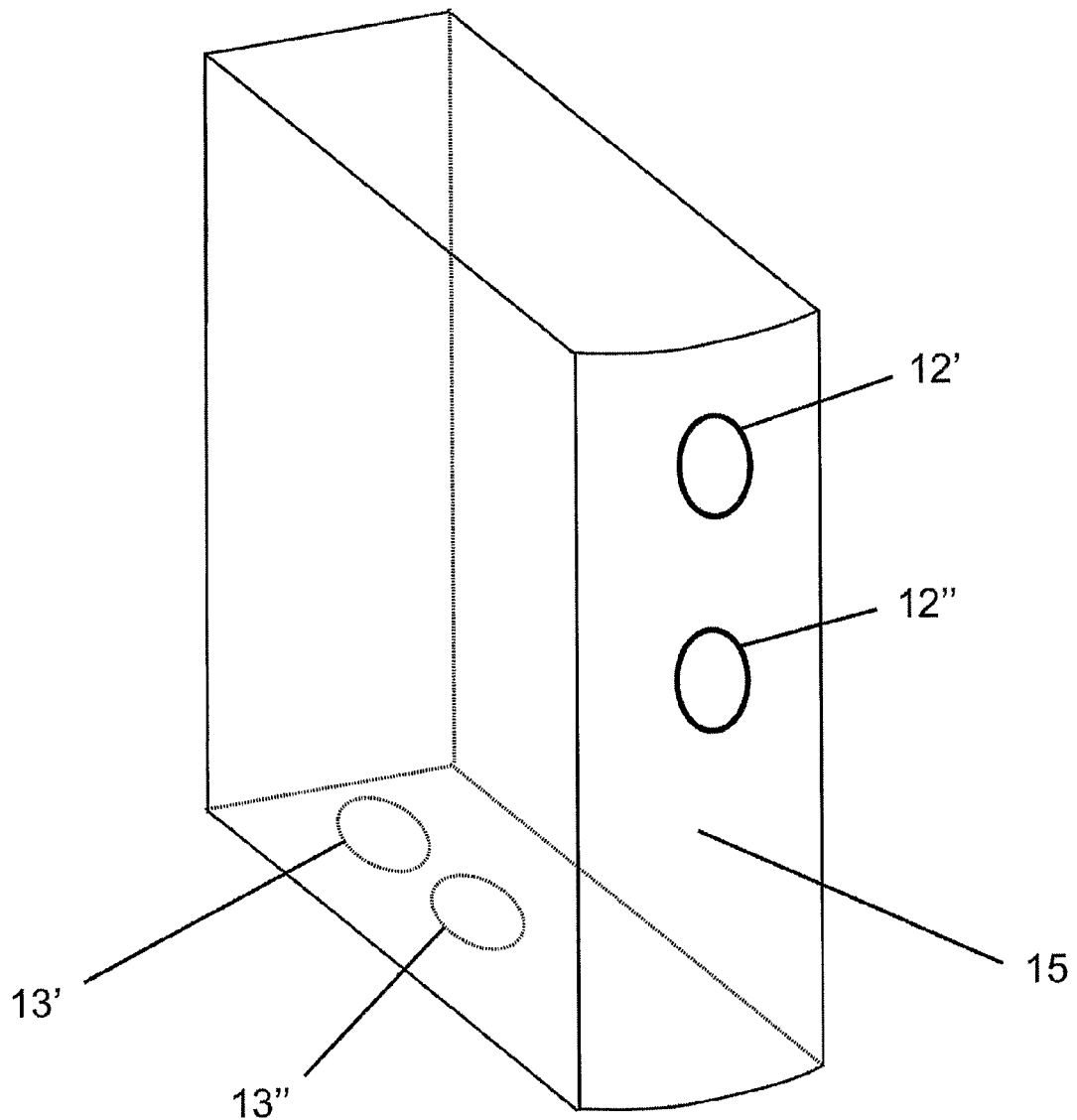
FIG. 6 represents the same as FIG. 5, but with a minimal distance between the two exiting holes of the electrode's wires.
Figure 7:
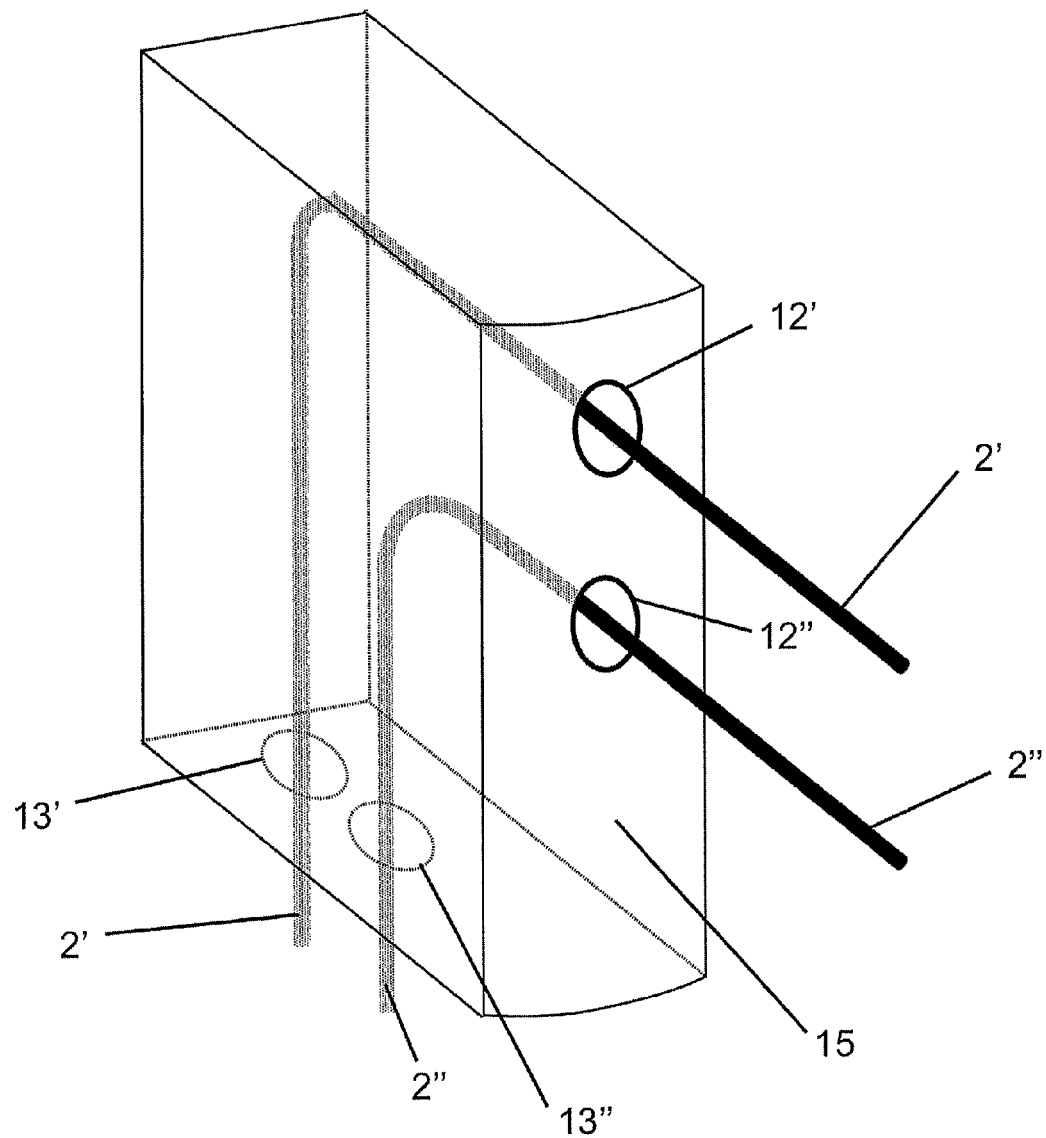
FIG. 7 represents a disposable part, with the two wires arriving by the entering holes above and protruding by the exiting holes.

FIG. 5 and FIG. 6 show the disposable part 15, outside the main body 1, and without the electrode's 2 two wires 2' and 2'', and with different distances between the two exiting holes 12' and 12''.

The disposable part 15 is inserted sterilized in the main body 1 before each procedure, and the choice of a disposable part 15, with a different distance between the two exiting holes 12' and 12'' allows the destruction of different sizes of tumors by the heating effect obtained at the distal parts 2''' and 2'''' of the two wires 2' and 2'', respectively.

The external shape of the disposable part 15 is exactly the same, even in different distances between the two exiting holes 12' and 12'', so to allow the insertion of the disposable part 15 in the main body.

FIG. 5 and FIG. 6 also show the two entry holes 13' and 13'', by which the canals 9 and 9' continue respectively from the main body 1 until the exiting holes 12' and 12'', respectively.

The distance between the two entry holes 13' and 13'' is always the same, even when disposable parts 15 with different distance between the two exiting holes 12' and 12'' are used.

Figure 12:
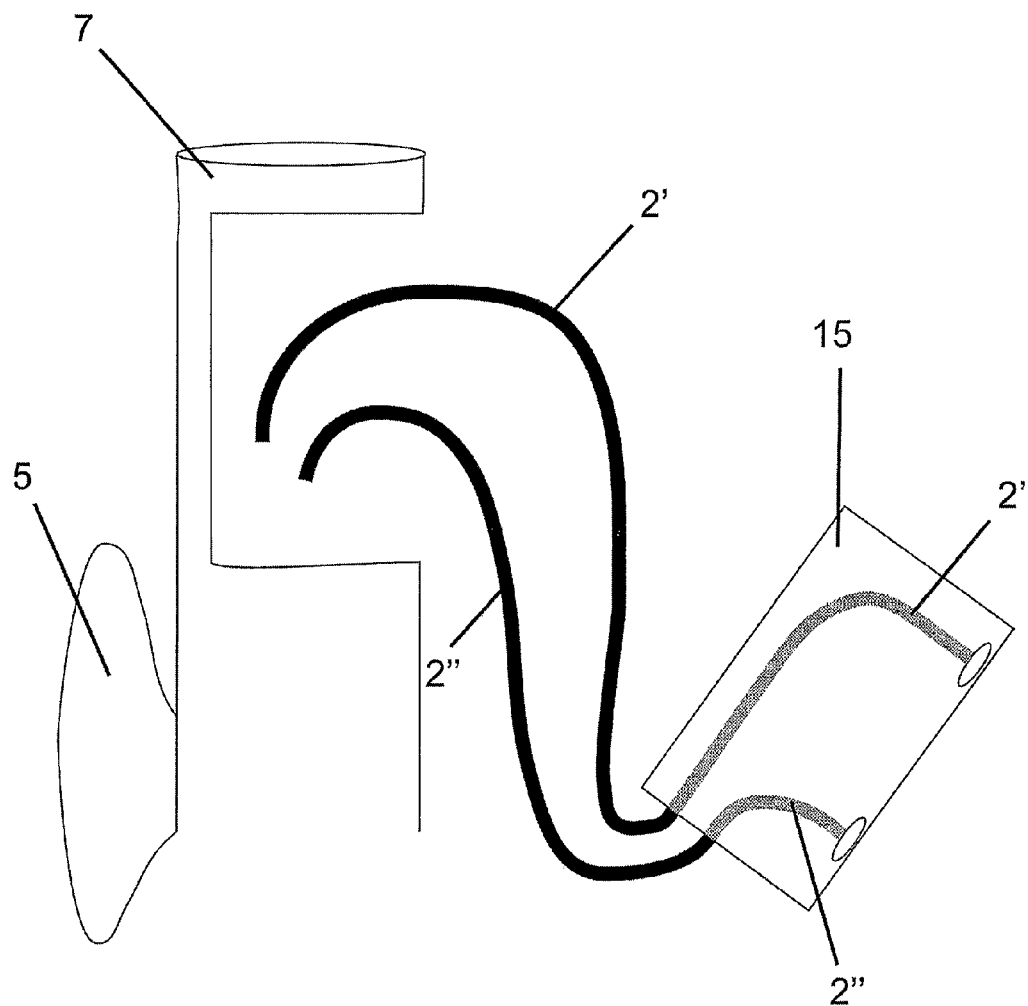
FIG. 12 represents the extraction of the disposable part (including the disposable wires), after the procedure.

FIG. 12 shows the simultaneous extraction of the disposable part 15, as well as of the two wires 2' and 2'', after each surgical procedure. The disposable part 15 as well as the two wires 2' and 2'' are disposable and replaced before each procedure.

The simultaneous extraction of the disposable part 15 and the two wires 2' and 2'' avoids the terminal parts of the two wires 2' and 2'' which have been in contact with tumoral tissue, to be in contact with any non disposable part, i.e. with the main body 1 and the parts of the two canals 9 and 9' crossing the main body 1.

The parts of the two wires 2' and 2'' that have been in contact with the tumoral tissue remain entirely in the part of the two canals 9 and 9' inserted in the disposable part 15.

Typically, four configurations are defined in the operation of the device:

1. Rest Configuration

The rest configuration is the configuration where the device is not placed inside the patient's body. In the rest configuration and before a surgical procedure the disposable part 15 is inserted in the main body 1, the control box 4 is connected to the main body 1, via the motor box tube 8, and the wires 2' and 2'' are inserted in the main body 1, via the insertion point 4'.

After the insertion of the two wires 2' and 2'' in the motor box 4, via the insertion point 4', the up sliding movement of the two wires 2' and 2'' are preferably controlled by the motors drives located inside the control box 4, after a command by the operator through the control panel 4''. At the rest configuration, the two wires 2' and 2'' do not protrude outside the main body 1, via the two exiting holes 13' and 13''.

At the end of the surgical procedure, the disposable part 15, with the two wires 2' and 2'' are removed and disposed of.

Before the removal of the disposable part 15, the two wires 2' and 2'' slide down inside the disposable part 15 and the main body 1.

2. Placement Configuration

The placement configuration is the configuration corresponding to the insertion of the device inside a human endocavity, like the bronchial tree, esophagus, or rectum, for example, until the distal end 7 reaches the wanted part of the considered endocavity.

In the placement configuration, the distal end 7 of the main body 1 has the following degrees of freedom, according to a referential system (0, X, Y, Z):

Translation along the Y axis.
Rotation around the Y axis.
Translation along the Z axis.

Figure 8:
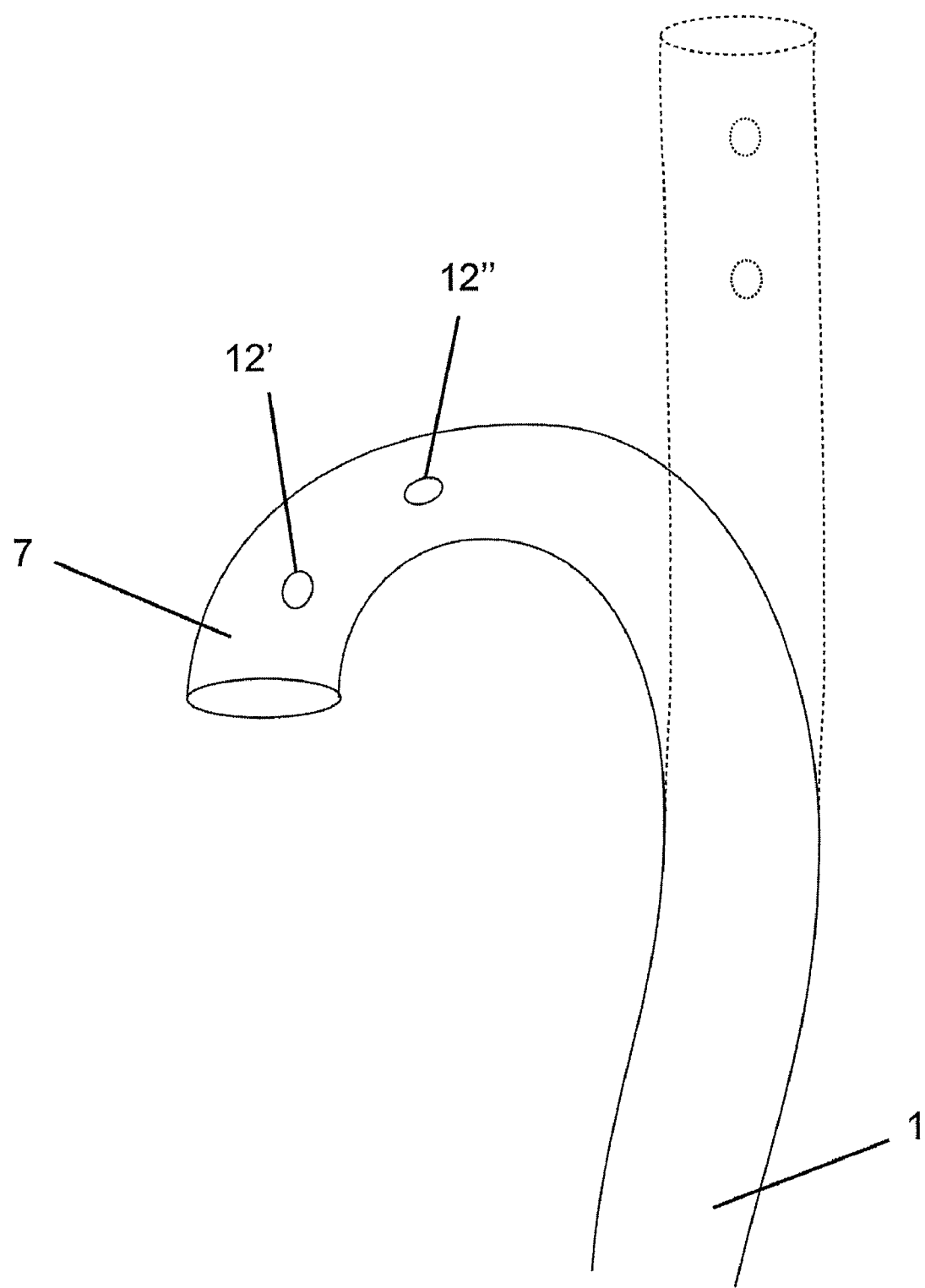
FIG. 8 represents the J shaped bending movement as described in the placement configuration.

The translation along the Z axis is gradually more important in more distal points of the distal end 7 of the main body 1, allowing the tip of the distal end 7 to do a J shaped movement, as showed in FIG. 8.

The translation along the Z axis is done in just one direction, i.e. with a 90 degree angle with the face of the disposable part 15 containing the exiting holes 12' and 12'', allowing a J shaped bending movement to be done with the exiting holes 12' and 12'' placed laterally, as showed in FIG. 8.

Both the translation along the Y axis and the rotation around the Y axis are controlled manually by the operator, via the direct manipulation of the proximal end 6 of the main body 1.

The translation along the Z axis, i.e. the J shaped movement of the distal end 7 of the main body 1, is controlled by the operator via the activation of the knobs 3' and 3'' placed in the proximal handle 3, situated in the proximal end 6 of the main body 1.

The two knobs 3' and 3'' control the movements of the two cables 10' and 10'', as showed in FIG. 13, called mobility 1.

At the end of the placement configuration, i.e. when the distal end 7 of the main body 1 is placed inside the wanted endocavity, using the three degrees of freedom described above, the mobility 1 knobs 3' and 3'' are activated by the operator one more time, until the distal end 7 of the main body 1 remains straight and stiff, i.e. with the two exiting holes 12' and 12'' remained perfectly aligned, allowing the two wires 2' and 2'' to exit from the disposable part 15, through the two exiting holes 12' and 12'', respectively, in a parallel way, (however, the two wires 2' and 2'' will only protrude from the disposable part 15 in the below described work configuration).

The placement configuration happens with the aid of a navigation system, that uses previously obtained pictures of the endocavity itself and of the tumor, to guide, via the magnetic coil 11, the distal end 7 of the main body 1 in the right part of the endocavity, like a. segmental bronchus, esophagus or rectum, for example.

3. Adjustment Configuration

The adjustment configuration is the configuration where the distal end 7 of the main body 1 is already placed in the wanted portion of the endocavity, as a segmental bronchus, or the esophagus, for example.

Figure 9:
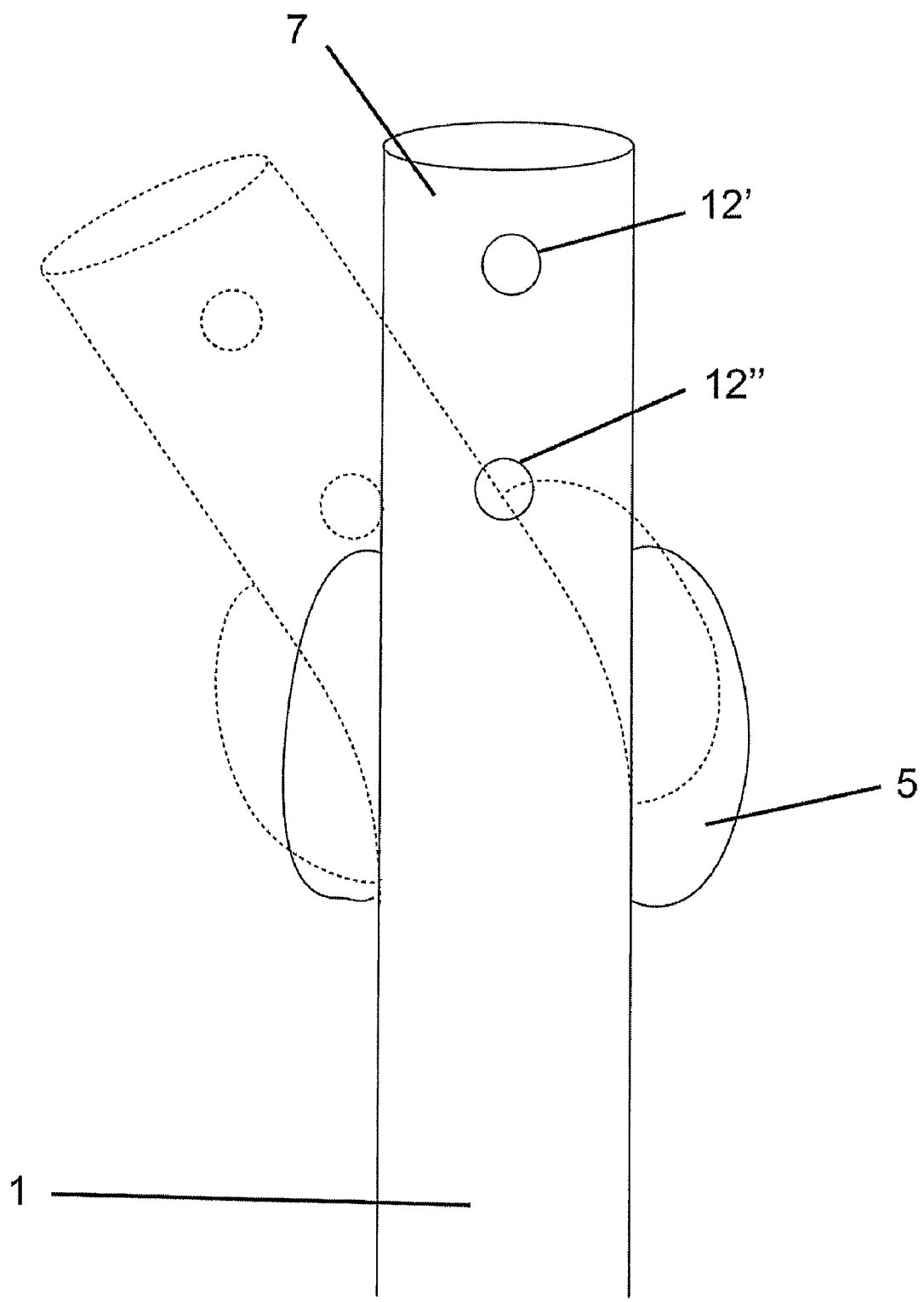
FIG. 9 represents the translation along X axis with the terminal end straight, as described in the adjustment configuration.

In the adjustment configuration, the straight distal end 7 of the main body 1 has the following degrees of freedom, according to a referential system (0, X, Y, Z):

Rotation, in the plan defined by the Y and Z axis, around a point in the main body 1 situated proximally from the straight distal end 7, as showed in FIG. 9.

Rotation around the Y axis.

Translation along the Y axis.

Both the translation along the Y axis and the rotation around the Y axis are controlled manually by the operator, via the direct manipulation of the proximal end 6 of the main body 1.

The rotation in the plan defined by the Y and Z axis, around a point in the main body 1 situated proximally from the straight distal end 7, is controlled by the operator via the activation of the knobs 3''' and 3'''' placed in the proximal handle 3, situated in the proximal end 6 of the main body 1.

The two knobs 3''' and 3'''' control the movements of the two cables 10''' and 10'''', as showed in FIG. 13, called mobility 2.

After the adjustment configuration movements have been achieved, the cuff 5, placed in the opposite face of the main body 1 from the exiting holes 12' and 12'', is inflated so to allow the aligned exiting holes 12' and 12'' to apply against the endocavity wall.

The adjustment configuration happens under a real time imaging system, like a CT scan or a ultrasound system, for example.

4. Working Configuration

The working configuration is the configuration where all the movements described above are locked, as the exiting holes 12' and 12'' are in the right position to allow the wires 2' and 2'' to protrude and penetrate correctly in the tumor 17, crossing the endocavity wall 18.

At this time, the motor drives inside the control box 4 are activated, so to allow the two wires 2' and 2'' to slide up inside the canals 9 and 9', respectively, until they protrude from the disposable part 15 by the two exiting holes 12' and 12'', respectively.

Figure 10:
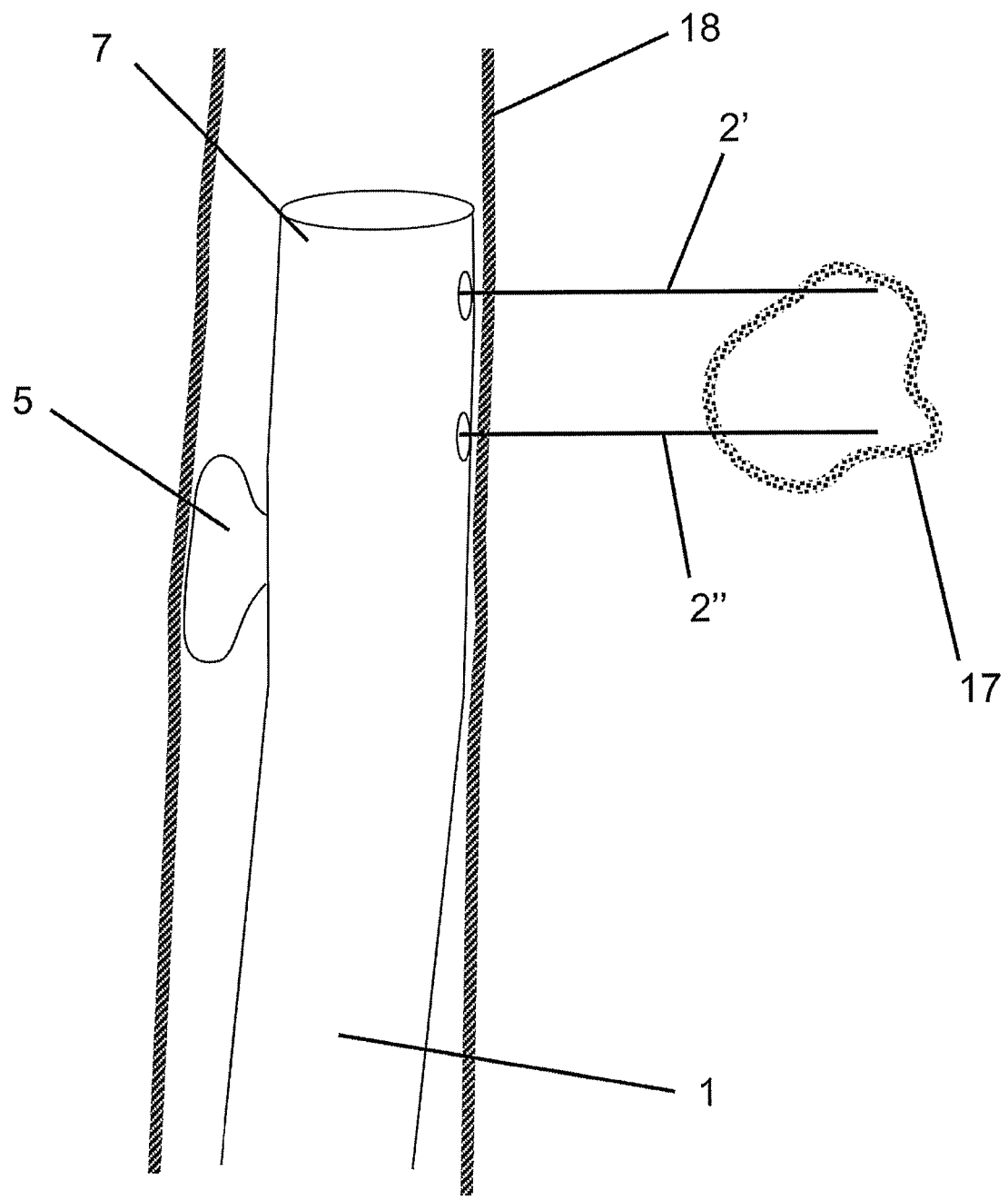
FIG. 10 represents the endoscope in operating position, with its electrode's wires inserted inside a tumor.
Figure 11:
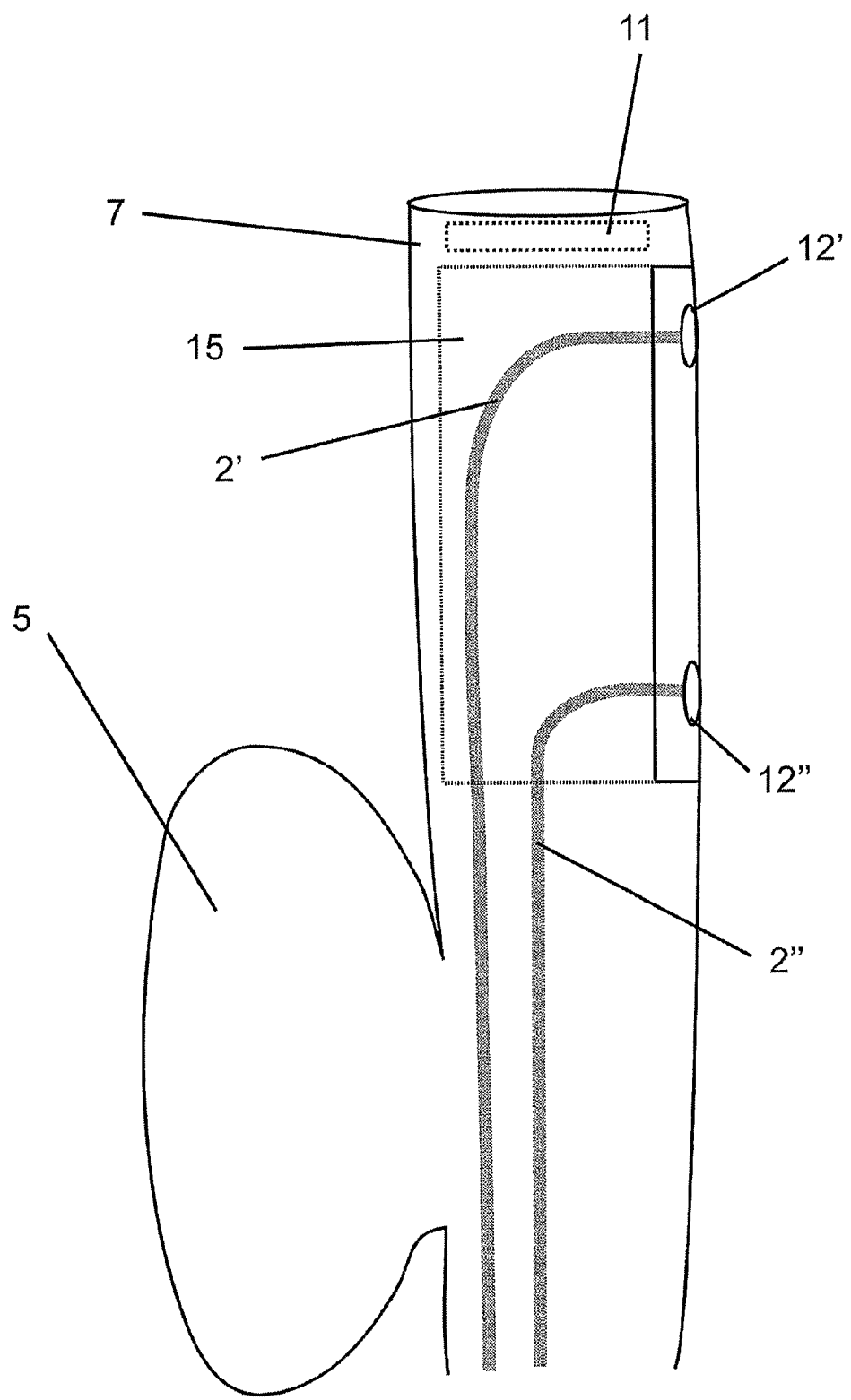
FIG. 11 represents the distal end of the instrument, with its wires placed, before or immediately after the operating position.

Once inside the tumor 17, the external radio frequency generator is activated, allowing a heating effect to happen in the distal parts 2''' and 2'''' of the two wires 2' and 2'', respectively, and destroying the tumor 17, as showed in FIG. 10.

The working configuration happens under a real time imaging system, lie a CT scan or a ultrasound system, for example.

What is claimed is:

1. A radio frequency treatment endoscope, comprising:
   a cylindrical and flexible elongated main body (1), said main body (1) having a distal end (7) and a proximal end (6) said distal end (7) comprising a recess;
   a disposable and interchangeable head (15), said head (15) being placed in said recess and not extending from said main body (1);
   at least two deployable, thin and elongated electrodes (2', 2''), said electrodes (2', 2'') being deployable laterally from and extending from said head (15) through at least two exiting holes (12', 12'') into a tissue; and
   an externally coupled radio frequency generator.

2. A radio frequency treatment endoscope system, comprising:
   a cylindrical and flexible elongated main body (1), said main body (1) having a distal end (7) and a proximal end (6) said distal end (7) comprising a recess;
   at least two deployable, thin and elongated electrodes (2', 2'');
   a plurality of disposable and interchangeable heads (15), having different variably spaced electrode exiting holes (12', 12''), allowing the electrodes (2', 2'') to deploy at a variable distance one from the other in order to fit a tumor's size and shape;
   wherein one of the plurality of heads (15) is placed in said recess and not extending from said main body (1);
   wherein said electrodes (2', 2'') are deployable laterally from and extending from the one of the plurality of heads (15) through at least two exiting holes (12', 12''); and
   an externally coupled radio frequency generator.

3. The radio frequency treatment endoscope according to claim 1:
   wherein the distal end (7) is capable of swiveling,
   said radio frequency treatment endoscope further comprising:
   a proximal end handle (3) with control knobs, and elongated wires placed in the main body (1) allowing the distal end (7) to be adjustably controlled and oriented.

4. The radio frequency treatment endoscope according to claim 1
   wherein the electrodes (2',2'') comprise:
   a polymeric insulating coating (16).

5. The radio frequency treatment endoscope according to claim 1
   wherein the elongated electrodes (2', 2'') are disposable and interchangeable.

6. The radio frequency treatment endoscope according to claim 1
   wherein the main body is connected to a control box (4), allowing a millimetric control of a motorized deployment of the elongated electrodes (2',2'') from the head (15) into a tissue and/or a tumor.

7. The radio frequency treatment endoscope according to claim 1, further comprising:
   a mechanical structure to control the deployment of the elongated electrodes (2', 2'') from the main body (1) through the head (15) and into the tissue, allowing near millimeter control of the electrodes' deployment, said mechanical structure being at the proximal end of the main body (1) and being controlled by the control knobs.

8. The radio frequency treatment endoscope according to claim 1
   wherein the proximal end (6) further comprises:
   a flexible and air expandable cuff (5) placed at the opposite site of the recess.

9. The radio frequency treatment endoscope according to claim 1, further comprising:
   several holes (21), operatively positioned near the electrodes' exiting holes (12',12''), and operatively connected to an external negative pressure generator.

10. The radio frequency treatment endoscope according to claim 1, further comprising:
    a magnetic coil (11) operatively positioned within the main the body's distal end, for allowing an external navigation/positioning system to define the device's tip location.

11. The radio frequency treatment endoscope according to claim 1, further comprising:
    a distal end placed optical based system, allowing, via an elongated fiberoptic pathway, the operator to see the tissue.

* * * * *